United States Patent [19]

Ohashi et al.

[11] 4,384,139

[45] May 17, 1983

[54] PROCESS FOR PREPARATION OF AN OPTICALLY ACTIVE β-MERCAPTOALKANOIC ACID

[75] Inventors: Takehisa Ohashi, Kobe; Masami Shimazaki, Takasago; Kenji Nomura; Kazunori Kan, both of Kobe; Kiyoshi Watanabe, Akashi, all of Japan

[73] Assignee: Kanegafuchi Chemical Industry Company, Limited, Osaka, Japan

[21] Appl. No.: 294,028

[22] Filed: Aug. 18, 1981

[30] Foreign Application Priority Data

Aug. 20, 1980 [JP] Japan .................. 55/115053

[51] Int. Cl.³ .......................................... C07C 51/363
[52] U.S. Cl. .............................. 562/512; 260/544 F; 260/544 X; 424/274; 562/401
[58] Field of Search ........................ 260/544 F, 544 X; 562/401, 512

[56] References Cited

U.S. PATENT DOCUMENTS

| | | | |
|---|---|---|---|
| 3,322,825 | 5/1967 | Fernholz et al. | 260/544 X |
| 3,449,416 | 6/1969 | Brotherton | 260/544 X |
| 3,517,058 | 6/1970 | Thoma et al. | 562/512 |
| 3,927,085 | 12/1975 | Zengel et al. | 562/512 |
| 4,129,595 | 12/1978 | Suzuki | 260/544 X |
| 4,224,457 | 9/1980 | Iwao et al. | 562/401 |
| 4,294,775 | 10/1981 | McKinnie et al. | 562/401 X |

FOREIGN PATENT DOCUMENTS 54-151911 11/1979 Japan .
55-20795 2/1980 Japan .

OTHER PUBLICATIONS

Compt. Rend., 174, 1173 (1922) [Chem. Abstr., 16, 2480 (1922)] E. E. Blaise and M. Montagne.
Compt. Rend., 174, 1553 (1922) [Chem. Abstr. 17, 3163 (1923)] E. E. Blaise and M. Montagne.
Chem. Ber., 39, 732 (1906) P. Klason and T. Carlson.
Methoden der Organischen Chemie (Houben–Weyl), vol. 9, pp. 7 et seq. (1955).

*Primary Examiner*—Glennon H. Hollrah
*Assistant Examiner*—Vera C. Clarke
*Attorney, Agent, or Firm*—Armstrong, Nikaido, Marmelstein & Kubovcik

[57] ABSTRACT

A process is disclosed wherein an optically active β-mercaptoalkanoic acid represented by formula (I):

$$HSCH_2\underset{R_1}{CH}CO_2H \qquad (I)$$

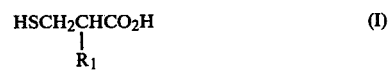

wherein $R_1$ is lower alkyl having from 1 to 4 carbon atoms, is prepared by (1) reacting an optically active β-hydroxyalkanoic acid represented by formula (II):

$$HOCH_2\underset{R_1}{CH}CO_2H \qquad (II)$$

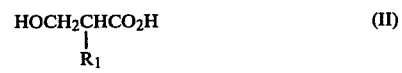

wherein $R_1$ is the same as defined above, with a halogenating reagent to prepare an optically active β-haloalkanoyl halide represented by formula (III):

$$XCH_2\underset{R_1}{CH}COX \qquad (III)$$

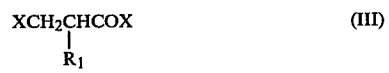

wherein X is halogen and $R_1$ is the same as defined above;

(2) reacting the β-haloalkanoyl halide with water or an aqueous alkaline solution to prepare an optically active β-haloalkanoic acid represented by formula (IV):

$$XCH_2\underset{R_1}{CH}CO_2H \qquad (IV)$$

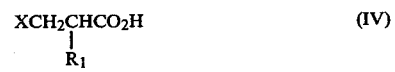

wherein X and $R_1$ are each the same as defined above, or a salt thereof, respectively; and (3) reacting the β-haloalkanoic acid or the salt thereof with a reagent capable of converting the halogen into the thiol group, the configuration of the compound (II), (III), and (IV) being retained throughout the process to prepare the compound represented by formula (I). The product of the present invention is useful as an intermediate for preparation of an antihypertensive agent such as N-(3-mercapto-2-D-methylpropanoyl)-L-proline.

18 Claims, No Drawings

PROCESS FOR PREPARATION OF AN OPTICALLY ACTIVE β-MERCAPTOALKANOIC ACID

BRIEF SUMMARY OF THE INVENTION

The present invention relates to a process for preparation of an optically active β-mercaptoalkanoic acid. More specifically, the present invention relates to a process for preparation of an optically active β-mercaptoalkanoic acid represented by formula (I):

$$\text{HSCH}_2\text{CHCO}_2\text{H} \quad\quad (I)$$
$$|$$
$$R_1$$

wherein $R_1$ is lower alkyl having from 1 to 4 carbon atoms, starting from an optically active β-hydroxyalkanoic acid represented by formula (II):

$$\text{HOCH}_2\text{CHCO}_2\text{H} \quad\quad (II)$$
$$|$$
$$R_1$$

wherein $R_1$ is the same as defined above.

The product of the present invention is a useful compound as an intermediate for preparation of an antihypertensive agent such as N-(3-mercapto-2-D-methyl-propanoyl)-L-proline which has already been put on the market in Europe. N-(3-mercapto-2-D-methyl-propanoyl)-L-proline, which has hitherto been prepared by processes involving troublesome optical resolution, is readily prepared by acylation of the compound (I) and succeeding coupling of the resulting product with L-proline followed by deacylation of the coupled product [D. W. Cushman, H. S. Cheung, E. F. Sabo, and M. A. Ondetti, Biochemistry, 16, 5484 (1977); M. A. Ondetti et al., U.S. Pat. Nos. 4,046,889 (1977), 4,105,776 (1978), 4,154,840 (1979)]. An optically active β-mercaptoalkanoic acid of formula (I) has hitherto not been prepared and only a racemic mixture of 3-mercapto-2-methylpropanoic acid was prepared by addition of hydrogen sulfide to methyl methacrylate followed by hydrolysis of the resulting ester [R. Tressel, M. Holzer, and M. Apetz, J. Agric, Food Chem., 25, 455 (1977)]. Therefore, to obtain an optically active 3-mercapto-2-methylpropanoic acid, this racemic mixture must be subjected to troublesome optical resolution.

The object of the present invention is therefore to provide an improved process for preparation of an optically active β-mercaptoalkanoic acid (I) starting from an optically active β-hydroxyalkanoic acid (II).

The present invention is a process for preparation of an optically active β-mercaptoalkanoic acid represented by formula (I):

$$\text{HSCH}_2\text{CHCO}_2\text{H} \quad\quad (I)$$
$$|$$
$$R_1$$

wherein $R_1$ is lower alkyl having from 1 to 4 carbon atoms, which comprises (1) reacting an optically active β-hydroxyalkanoic acid represented by formula (II):

$$\text{HOCH}_2\text{CHCO}_2\text{H} \quad\quad (II)$$
$$|$$
$$R_1$$

wherein $R_1$ is the same as defined above, with a halogenating reagent to prepare an optically active β-haloalkanoyl halide represented by formula (III):

$$\text{XCH}_2\text{CHCOX} \quad\quad (III)$$
$$|$$
$$R_1$$

wherein X is halogen and $R_1$ is the same as defined above;

(2) reacting the β-haloalkanoyl halide with water or an aqueous alkaline solution to prepare an optically active β-haloalkanoic acid represented by formula (IV):

$$\text{XCH}_2\text{CHCO}_2\text{H} \quad\quad (IV)$$
$$|$$
$$R_1$$

wherein X and $R_1$ are each the same as defined above or a salt thereof, respectively; and (3) reacting the β-haloalkanoic acid with a reagent capable of converting the halogen into the thiol group, the configuration of the compound (II), (III) and (IV) being retained throughout the process to prepare the compound represented by formula (I).

According to the process of the present invention, an optically active β-mercaptoalkanoic acid (I) can be obtained from a starting optically active β-hydroxyalkanoic acid (II) in a facile process involving no troublesome optical resolution. It is an advantageous feature of the present invention that the configuration of all the optically active compounds involved in the process is completely retained throughout the process.

The starting material of the present invention, the compound (II), has come to be produced industrially according to inventions by some of the present inventors in which the compound (II) is produced by subjecting the corresponding alkanoic acid to the stereospecific action of microorganisms. In particular, the compound (II) in which $R_1$ is methyl can be produced by subjecting isobutyric acid or methacrylic acid to the stereospecific action of specific microorganisms (U.S. patent application Ser. No. 201,337; Japanese patent applications Nos. 140258/1980, 140259/1980, and 141453/1980).

In one aspect, therefore, the present invention is very advantageous in that the starting material is readily available industrially and the optical activity thereof can be retained to produce the desired optically active product. Thus, the present invention had eliminated the foregoing drawbacks in the known processes, providing an advantageous process for preparing an optically active β-mercaptoalkanoic acid (I).

Concerning halogenation of β-hydroxyalkanoic acid which relates to the first step of the process of the present invention, it was reported that thionyl chloride was allowed to act on α-hydroxyisobutyric acid [E. E. Blaise and M. Montagne, Compt, rend., 174, 1553 (1922)]; however, the product of the reaction was not α-chloroisobutyryl chloride but was anhydrosulfite of α-hydroxyisobutyric acid, and moreover, there is no description about optical activity in the report. In another report [E. L. Eliel et al., Org. Synth., Coll. Vol. IV, P. 169 (1963)], optically active α-chlorophenylacetic acid was produced from mandelic acid according to a two-step process in which the carboxyl group was first protected by esterification with ethanol, and then halogenation with thionyl chloride was conducted, the aimed free acid being finally obtained by hydrolysis of the ester group.

In contrast with these known halogenation of hydroxyalkanoic acid, it is to be noted that, in the process of the present invention, halogenation of an optically active β-hydroxyalkanoic acid (II) is performed on both hydroxyl group and the carboxyl group in one step with retention of the configuration to produce an optically active β-haloalkanoyl halide (III).

In the next step, an optically active β-haloalkanoic acid (IV) or a salt thereof is prepared from an optically active β-haloalkanoyl halide (III). An optically active β-haloalkanoic acid (IV) has hitherto not been prepared; only a racemic mixture of 3-chloro-2-methylpropanoic acid has been prepared by addition of hydrogen chloride to methacrylic acid [M. G. Lin'Kova, et al., Izv. Akad, Nauk SSSR, Ser. Khim., 1886 (1968); Chem. Abstr., 70, 3223f (1969)].

According to the process of the present invention, an optically active β-haloalkanoyl halide (III) is treated with water or an aqueous alkaline solution; such as an aqueous solution of an alkali or alkaline earth metal or ammonium hydroxide, carbonate, bicarbonate, borate, or phosphate; to prepare an optically active β-haloalkanoic acid (IV) or a salt thereof, respectively.

The conversion of the halogen in the compound (IV) or a salt thereof into the thiol group in the third step of the process of the present invention is conducted with the usual reagents capable of converting the halogen into the thiol group [P. Klason and T. Carlson, Chem. Ber., 39, 732 (1906); For a review of the reaction, see Methoden der Organischen Chemie (Houben-Weyl), Vol. 9, p, 7 et seq. (1955)]. On the other hand, however, there are no reports on the application of such reagents to the conversion of a halogen into the thiol group in an optically active compound such as the compound (IV) of the process of the present invention. In general, the reagent, e.g., sodium hydrosulfide or ammonium hydrosulfide, is strongly alkaline in solution and therefore no one has ever tried the application of the reagents to an optically active compound because racemization is expected to take place readily under such alkaline conditions.

Nevertheless, the present inventors havve surprisingly found that the optical activity is retained completely in the reaction of the compound (IV) with an alkaline reagent such as sodium hydrosulfide and ammonium hydrosulfide, and moreover, the side reactions can be minimized by adopting an optimum molar ratio of the reagent to the compound (IV) or a salt thereof.

DETAILED DESCRIPTION OF THE INVENTION

The lower alkyl group having from 1 to 4 carbon atoms represented by $R_1$ in compounds (I), (II), (III), and (IV) includes straight and branched chain hydrocarbon groups such as methyl, ethyl, propyl, isopropyl, butyl, isobutyl, t-butyl and so forth.

According to the process of the present invention, an optically active β-hydroxyalkanoic acid (II) can readily be converted into an optically active β-haloalkanoyl halide (III) with retention of the optical activity in a one-step reaction as described hereinbefore. As described in comparison with known methods for halogenation of hydroxyalkanoic acid, this step in the process of the present invention is the first facile method for preparing an optically active β-haloalkanoyl halide from an optically active β-hydroxyalkanoic acid with retention of the optical activity in a one step reaction.

The halogenation of the optically active β-hydroxyalkanoic acid (II) is conducted preferably in the presence of a catalyst such as an organic amine, acid addition salt thereof, or organic acid amide. As the organic amine, there can be used, for example, methylamine, dimethylamine, trimethylamine, ethylamine, diethylamine, triethylamine, imidazole, piperidine, morpholine, pyridine, N,N-dimethylaniline, or N,N-diethylaniline. Imidazole is the most preferable among these. A hydrochloride, hydrobromide, sulfate, or phosphate can be used as an acid addition salt of the organic amine. As the organic acid amide, there can be is used, for example, formamide, N-methylformamide, N,N-dimethylformamide, acetamide, N,N-dimetylacetamide, N-formylmorpholine, or N-formylpiperidine. In the halogenation, the molar ratio of the catalyst to the β-hydroxyalkanoic acid (II) is from about 0.0001 to about 0.1, preferably from about 0.0001 to about 0.05. The halogenating reagent can be, for example, thionyl halide such as thionyl chloride and thionyl bromide, phosphorus trihalide such as phosphorus trichloride, phosphorus pentahalide such as phosphorus pentachloride, phosphorus oxychloride, oxalyl halide such as oxalyl chloride, and phosgene. Of these halogenating reagents, thionyl halide, such as thionyl chloride and thionyl bromide, is particularly preferred.

The molar ratio of thionyl halide to β-hydroxyalkanoic acid (II) can be from about 2 to about 3, preferably from about 2 to about 2.4. The halogenation can be conducted in the absence of a solvent, but the use of an inert organic solvent, such as diethyl ether, tetrahydrofuran, methylene chloride, ethylene dichloride, chloroform, carbon tetrachloride, benzene, or toluene makes the reaction controllable. In the halogenation, the temperature control is important to minimize side reactions and to retain the configuration of the starting β-hydroxyalkanoic acid (II). The reactants, for example, thionyl halide and the compound (II) are mixed while the temperature of the reaction mixture is kept at not more than 25° C. Then, after completion of the mixing, the reaction mixture is allowed to warm up to an ambient temperature with stirring and kept at that temperature until evolution of gaseous hydrogen halide and sulfur dioxide subsides. The desired compound (III) is isolable by the usual distillation under reduced pressure, or hydrolyzed directly with water or an aqueous alkaline solution without isolation to the compound (IV).

We have found that a rate-determining step in the halogenation of the compound (III) is decomposition of a nonisolable, unstable intermediate, β-halosulfonyloxylalkanoyl halide represented by formula (V):

(V)

wherein X and $R_1$ are each the same as defined above, and which is readily converted into the compound (III) by thermal decomposition, preferably under reduced pressure as when the compound (III) is distilled off, liberating sulfur dioxide. Therefore, when the compound (III) is directly subjected to the next reaction without isolation, after completion of the mixing of both the reactants, the temperature of the resulting reaction mixture is raised up to from about 30° C. to about 100° C., preferably from about 70° C. to about 80° C., to complete the decomposition of the compound (V) providing the desired compound (III).

The thermal treatment after completion of the mixing of both the reactants described above is an advantageous embodiment of the present invention in that the product of the halogenation, an optically active β-haloalkanoyl halide (III), need not be isolated but can be converted into the compound (IV) or a salt thereof by direct hydrolysis with water or the foregoing aqueous alkaline solution after removal of a solvent, if used, and an excess of thionyl halide.

An alkali metal, alkaline earth metal, ammonium, or organic base salt of the compound (II) can also be used as a starting material for the halogenation.

The resulting aqueous solution of an optically active β-haloalkanoic acid (IV) or a salt thereof is then subjected to substitution of the halogen by the thiol group, yielding the desired product of the present invention, an optically active β-mercaptoalkanoic acid (I). Thus, it is an advantageous feature of the present invention that the desired optically active β-mercaptoalkanoic acid (I) is prepared by so-called one pot reaction from the starting optically active β-hydroxyalkanoic acid (II) without isolation of intermediates, β-haloalkanoyl halide (III) and β-haloalkanoic acid (IV).

The reagent capable of converting the halogen into the thiol group can be, for example, a salt of hydrogen sulfide with an alkali or alkaline earth metal, ammonia, or an organic base, preferably sodium or ammonium hydrosulfide. The organic base includes methylamine, dimethylamine, trimethylamine, ethylamine, diethylamine, triethylamine, pyridine, piperidine, morpholine, imidazole, N,N-dimethylaniline, N,N-diethylaniline and so forth. Methylamine is preferable among the organic bases.

Substitution of the halogen by the thiol group is carried out in water or in a polar aprotic solvent such as dimethyl sulfoxide; N,N-dimethylformamide; and N,N-dimethylacetamide. The reagents described above, which are capable of converting the halogen into the thiol group, are all strongly alkaline in water or in the polar aprotic solvent, but neither the compound (IV) nor the compound (I) undergoes racemization in this reaction. This is noteworthy since an optically active compound generally undergoes racemization in an alkaline solution, especially on warming as is the case with the present invention. There have thus far been no reports on substitution of a halogen atom in an optically active compound by a salt of hydrogen sulfide.

The desired product of this invention, the compound (I), obtained in the foregoing final step of the process, is liable to be oxidized to give the disulfide represented by the following formula:

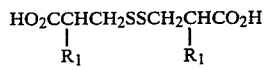

wherein $R_1$ is the same as defined above, which can be reverted to the thiol compound (I) by treatment with the usual reducing reagent, e.g., zinc powder in a dilute mineral acid or sodium hydrosulfite.

We have found that the side reaction can be averted by adopting an optimum molar ratio of the salt of hydrogen sulfide to the β-haloalkanoic acid (IV). The optimum molar ratio is from about 1 to about 10, preferably from about 1 to about 6.

The concentration of the salt of hydrogen sulfide in the reaction system is also an important factor in minimizing the amount of by-products. The optimum concentration is from about 5 wt% to about 10 wt%. The reaction in an inert gas atmosphere is effective in minimizing the amount of the disulfide described above. The reaction is carried out at a temperature of from about 30° C. to about 100° C., preferably from about 60° C. to about 90° C., under which conditions no racemization occurs.

According to a preferred procedure for preparing the compound of formula (I), especially when $R_1$ is methyl and X is chlorine, a β-hydroxyalkanoic acid of formula (II) is halogenated with thionyl halide, preferably thionyl chloride, in an anhydrous inert organic solvent, preferably methylene chloride, in the presence of a catalyst, preferably imidazole, of which the molar ratio to the acid of formula (II) is from about 0.0001 to about 0.1 by keeping the temperature of the reaction mixture at not more than 25° C. during the addition of the thionyl halide to the acid of formula (II) followed by allowing the reaction mixture to be stirred at an ambient temperature for about an hour, whereupon the evolution of hydrogen halide and sulfur dioxide subsides. The halide of formula (III) is isolated from the reaction mixture by distillation under reduced pressure and then hydrolyzed with water or an aqueous alkaline solution, preferably, of sodium bicarbonate at an ambient temperature to prepare a β-haloalkanoic acid of formula (IV) or a salt thereof. Subsequently, the reaction mixture, after neutralization with an aqueous alkaline solution, preferably an aqueous solution of sodium hydroxide or ammonium hydroxide, is reacted with a reagent capable of converting the halogen into the thiol group, preferably sodium hydrosulfide or ammonium hydrosulfide, of which the molar ratio to the β-haloalkanoic acid (IV) is from about 1 to about 6, in water or a polar aprotic solvent, preferably in water, at a temperature of from about 60° C. to about 90° C. to produce an optically active β-mercaptoalkanoic acid of formula (I).

According to a particularly preferred procedure for preparing the compound of formula (I), especially when $R_1$ is methyl and X is chlorine, β-hydroxyalkanoic acid of formula (II) is reacted with thionyl halide, preferably thionyl chloride, in the presence of a catalyst, preferably imidazole, in the absence of a solvent. In this case, the compound of formula (II) is added to thionyl chloride. The molar ratio of the catalyst to the acid of formula (II) is from about 0.0001 to about 0.05. The temperature of the reaction mixture is kept at not more than 25° C. during the addition of the acid of formula (II) and, after completion of the mixing of both the reactants, the temperature is raised up to from about 30° C. to about 100° C., preferably from about 70° C. to about 80° C., to complete the conversion of the intermediate (IV) into the compound of formula (III). The complete conversion is detected by observing the NMR spectrum of the reaction mixture. The halide of formula (III) is then hydrolyzed, without isolation, with water or an aqueous alkaline solution, for example, an aqueous solution of sodium bicarbonate, to prepare a β-haloalkanoic acid of formula (IV) or the corresponding salt thereof. Subsequently, the reaction mixture, after neutralization with an aqueous alkaline solution, preferably an aqueous solution of sodium or ammonium hydroxide, is subjected to substitution of the halogen by the thiol group with a reagent capable of converting the halogen into the thiol group, preferably sodium hydrosulfide or ammonium hydrosulfide, of which the molar ratio to the β-haloalkanoic acid of formula (IV) is from about 1 to about 6, at a temperature of from about 60° C. to about 90° C. to produce an optically active β-mercaptoalkanoic acid of formula (I).

To further illustrate the present invention, and not by way of limitation, the following examples are given.

EXAMPLE 1

3-Chloro-2-D-methylpropanoyl chloride

To a mixture of 3-hydroxy-2-D-methylpropanoic acid (36.6 g) and N,N-dimethylformamide (1.28 g), thionyl chloride (92.0 g) was added by drops with stirring over a period of 90 min, while the temperature of the reaction mixture was kept at not more than 25° C. by cooling in an ice-water bath. The reaction mixture was then warmed up to 40° C. and kept at that temperature for 1 hr. After removal of an excess of thionyl chloride by evaporation in a vacuum, 3-chloro-2-D-methylpropanoyl chloride was obtained as a colorless liquid by distillation under reduced pressure (32.1 g, 65%). bp 53°~54° C./21 mmHg. $[\alpha]_D^{25} -4.8°$ (C2.0, CH$_2$Cl$_2$).

EXAMPLE 2

3-Chloro-2-D-methylpropanoyl chloride

A solution of 3-hydroxy-2-D-methylpropanoic acid (10.4 g) in methylene chloride (10 ml) containing imidazole (0.5 g) as catalyst was added by drops to thionyl chloride (30 g) with stirring at a temperature of from about 0° C. to about 15° C. The reaction mixture was worked up in the same manner as in Example I, yielding 3-chloro-2-D-methylpropanyl chloride (11.7 g, 83%). bp 65°~67° C./34 mmHg.

EXAMPLE 3

3-Chloro-2-D-methylpropanoyl chloride

By substituting toluene for methylene chloride and heating the reaction mixture at a temperature of 80° C. for 3 hr after addition of thionyl chloride in the procedure of Example 2, 3-chloro-2-D-methylpropanyl chloride was obtained (85%).

EXAMPLE 4

3-Bromo-2-D-methylpropanoyl bromide

By substituting thionyl bromide for thionyl chloride in the procedure of Example 3, 3-bromo-2-D-methylpropanoyl bromide was obtained.

EXAMPLE 5

3-Chloro-2-L-methylpropanoyl chloride

By substituting the L-enantiomer for 3-hydroxy-2-D-methylpropanoic acid in the procedure of Example 2, 3-chloro-2-L-methylpropanoyl halide was obtained. $[\alpha]_D^{25} +4.7°$ (C2.0, CH$_2$Cl$_2$).

EXAMPLE 6

3-Chloro-2-L-ethylpropanoyl chloride

By substituting 3-hydroxy-2-L-ethylpropanoic acid for 3-hydroxy-2-D-methylpropanoic acid in the procedure of Example 2, 3-chloro-2-L-ethylpropanoyl chloride was obtained. bp 50°~52° C./40 mmHg. $[\alpha]_D^{25} -3.8°$ (C2.0, CH$_2$Cl$_2$).

EXAMPLE 7

3-Chloro-2-D-ethylpropanoyl chloride

By substituting 3-hydroxy-2-D-ethylpropanoic acid for 3-hydroxy-2-D-methylpropanoic acid in the procedure of Example 2, 3-chloro-2-D-ethylpropanoyl chloride was obtained. $[\alpha]_D^{25} +3.8°$ (C2.0, CH$_2$Cl$_2$).

EXAMPLE 8

3-Chloro-2-D-methylpropanoic acid

3-Chloro-2-D-methylpropanoyl chloride (5.35 g) was added in one portion to water (80 ml) and stirred at an ambient temperature for 4 hours, during which period the temperature of the reaction mixture rose up to about 40° C. in the early stage and then gradually fell to an ambient temperature. The reaction mixture became a clear homogeous solution and thin layer chromatography showed only one product. The product was extracted with ethyl acetate (100 ml + 50 ml) at pH 1 (6 N Hcl) and the extract was washed successively with an aqueous sodium chloride solution and water, dried over MgSO$_4$. Removal of the organic solvent left a syrup of 3-chloro-2-D-methylpropanoic acid (4.46 g, 96%). An analytical sample was obtained by distillation under reduced pressure. bp 91°~92° C./9 mmHg. $[\alpha]_D^{25} -13.2°$ (C4, MeOH). $n_D^{25}$ 1.4430.

EXAMPLE 9

3-Chloro-2-L-methylpropanoic acid

3-Chloro-2-L-methylpropanoyl chloride (5.35 g) was treated with NaHCO$_3$ (7 g) in water (100 ml) for 3 hours at an ambient temperature. The product was isolated in the same manner as in Example 8 to give a colorless liquid of 3-chloro-2-L-methylpropanoic acid (4.42 g, 95%).

EXAMPLE 10

3-Chloro-2-D-ethylpropanoic acid

By substituting 3-chloro-2-D-ethylpropanoyl chloride for 3-chloro-2-D-methylpropanoyl chloride in the procedure of Example 8, 3-chloro-2-D-ethylpropanoic acid was obtained.

EXAMPLE 11

3-Chloro-2-L-ethylpropanoic acid

By substituting 3-chloro-2-L-ethylpropanoyl chloride for 3-chloro-2-D-methylpropanoyl chloride in the procedure of Example 8, 3-chloro-2-L-ethylpropanoic acid was obtained.

EXAMPLE 12

3-Mercapto-2-D-methylpropanoic acid

A mixture of 3-chloro-2-D-methylpropanoic acid (1.5 g) and sodium hydrosulfide (4.5 g) in water (40 ml) was heated at 80° C. for 7 hours under a nitrogen atmosphere. The reaction mixture was cooled to room temperature, adjusted to pH2 with phosphoric acid, and the product was extracted with ethyl acetate (total 80 ml, twice). The extract was washed with a saturated aqueous solution of sodium chloride and dried over anhydrous Na$_2$SO$_4$. Removal of the solvent from the extract left a pale yellow oil (1.4 g). The oil was then dissolved in 1 N H$_2$SO$_4$ (20 ml) and treated with zinc powder (1.5 g) under a nitrogen atmosphere by stirring at room temperature for 5 hours, whereby the by-produced disulfide (ca. 10 mole%) was reduced to 3-mercapto-2-D-methylpropanoic acid. Insoluble materials were filtered off and washed with ethyl acetate. The filtrate and washings were combined and extracted with ethyl acetate (50 ml×3). The ethyl acetate extract was washed with a saturated aqueous solution of sodium chloride and dried over MgSO$_4$. Removal of the solvent from the extract left a colorless syrup of 3-mercapto-2-D-methylpropanoic acid (1.25 g, 85%). $[\alpha]_D^{25}$ −26.5° (C3, MeOH). $n_D^{20}$ 1.4818.

EXAMPLE 13

3-Mercapto-2-D-methylpropanoic acid

3-Chloro-2-D-methylpropanoic acid (7.9 g) was added to an aqueous solution of ammonium hydrosulfide, which had been prepared by dissolving hydrogen sulfide (15.9 g) in an aqueous ammonia (ca. 3.8 wt%, 270 ml) at room temperature. The resulting solution was stirred at 78° C. for 5 hours under a nitrogen atmosphere, whereupon no starting halide was detected on the NMR spectrum (The conversion of the halide into the thiol compound was followed by observing the NMR spectrum at intervals). The reaction mixture was then concentrated to about 50 ml and adjusted to become a 1 N H$_2$SO$_4$ solution by adding conc, H$_2$SO$_4$. The resulting solution was treated with zinc powder (3 g) as reducing agent by stirring at room temperature for 5 hours under a nitrogen atmosphere. The product was then isolated in the same manner as in Example 12 to give a colorless syrup (7.0 g, 91%). bp 62°~63° C./1 mmHg. $[\alpha]_D^{25}$ −26.6° (C3, MeOH).

EXAMPLE 14

3-Mercapto-2-L-methylpropanoic acid

By substituting 3-chloro-2-L-methylpropanoic acid, which is prepared from 3-chloro-2-L-methylpropanoyl chloride in the same manner as in Example 8, for 3-chloro-2-D-methylpropanoic acid in the procedure of Example 13, 3-mercapto-2-L-methylpropanoic acid was obtained. $[\alpha]_D^{25}$ +26.6° (C3, MeOH).

EXAMPLE 15

3-Mercapto-2-D-methylpropanoic acid from 3-chloro-2-D-methylpropanoyl chloride 3-Chloro-2-D-methylpropanoic acid was obtained as an aqueous solution by hydrolysis of 3-chloro-2-D-methylpropanoyl chloride (5.35 g) in the procedure of Example 8, and to this aqueous solution was added 6 N NaOH (1 eq.). To the resulting neutral solution was added sodium hydrosulfide (4.55 g) and stirred at 80° C. for 8 hours under a nitrogen atmosphere, whereupon the pH of the solution was 8.7. The rection mixture was worked up in the same manner as in Example 12, giving a syrup of 3-mercapto-2-D-methylpropanoic acid (3.53 g, 80%).

EXAMPLE 16

3-Mercapto-2-D-methylpropanoic acid from 3-hydroxy-2-D-methylpropanoic acid

3-Hydroxy-2-D-methylpropanoic acid (10.4 g) in methylene chloride (10 ml) was reacted with thionyl chloride (19.1 ml) at 0°~5° C. in the presence of imidazole (68 mg) for half an hour and then warmed at 80° C. for 3 hours, while methylene chloride and excessive thionyl chloride were removed from the reaction mixture. The cooled reaction mixture was then treated with water (60 ml) for 4 hours, followed by neutralization with 10% NaOH (40 ml). To this solution was added 10 N NH$_4$OH (60 ml), and hydrogen sulfide (13 g) was absorbed by bubbling into the solution at room temperature. The resulting solution was then stirred at 80° C. for 2 hours and worked up in the same manner as in Example 13, giving a colorless syrup of 3-mercapto-2-D-methylpropanoic acid (8.17 g, 68%). bp. 68° C./0.2 mmHg.

EXAMPLE 17

3-Mercapto-2-D-ethylpropanoic acid

By substituting 3-chloro-2-D-ethylpropanoic acid for 3-chloro-2-D-methylpropanoic acid in the procedure of Example 12, 3-mercapto-2-D-ethylpropanoic acid was obtained.

EXAMPLE 18

3-Mercapto-2-L-ethylpropanoic acid

By substituting 3-chloro-2-L-ethylpropanoic acid for 3-chloro-2-D-methylpropanoic acid in the procedure of Example 12, 3-mercapto-2-L-ethylpropanoic acid was obtained.

In addition to the reactants and conditions used in the foregoing examples, other reactants and conditions as set forth in the specification may also be used to obtain substantially the same results.

What is claimed is:

1. A process for preparing an optically active β-mercaptoalkanoic acid represented by formula (I):

wherein R$_1$ is lower alkyl having from 1 to 4 carbon atoms, which comprises (1) reacting an optically active β-hydroxyalkanoic acid represented by formula (II):

wherein R$_1$ is the same as defined above, with thionyl chloride or thionyl bromide in the presence of a catalyst by keeping the temperature of the reaction mixture at not more than 25° C. when thionyl chloride or thionyl bromide is mixed with the compound (II) and then raising the temperature of the reaction mixture up to from about 30° C. to about 100° C. to prepare an optically active β-haloalkanoyl halide represented by formula (III):

wherein X is chlorine or bromine and R$_1$ is the same as defined above;

(2) reacting the β-haloalkanoyl halide with water or an aqueous alkaline solution to prepare an optically active β-haloalkanoic acid represented by formula (IV):

$$XCH_2\underset{R_1}{\underset{|}{C}}HCO_2H \qquad (IV)$$

wherein X and $R_1$ are each the same as defined above, or a salt thereof, respectively; and (3) reacting the β-haloalkanoic acid or the salt thereof with an alkali metal salt of hydrogen sulfide or ammonium hydrogen sulfide, of which the molar ratio to the compound (IV) is from about 1 to about 10 and of which the concentration in the reaction system is from about 5 wt% to about 10 wt%, in water or a polar aprotic solvent at a temperature of from about 30° C. to about 100° C., the configuration of the compound (II), (III) and (IV) being retained throughout the process to prepare the compound represented by formula (I).

2. The process according to claim 1 wherein $R_1$ is methyl.

3. The process according to claim 1 wherein X is chlorine.

4. The process according to claim 1 wherein the molar ratio of the catalyst to the compound (II) is from about 0.0001 to about 0.1.

5. The process according to claim 1 wherein the catalyst is an organic amine or an acid addition salt thereof.

6. The process according to claim 6 wherein the organic amine is methylamine, dimethylamine, trimethylamine, ethylamine, diethylamine, triethylamine, imidazole, piperidine, morpholine, pyridine, N,N-dimethylaniline, or N,N-diethylaniline.

7. The process according to claim 1 wherein the catalyst is an organic acid amide.

8. The process according to claim 7 wherein the organic acid amide is formamide, N-methylformamide, N,N-dimethylformamide, acetamide, N,N-dimethylacetamide, N-formylmorpholine, or N-formylpiperidine.

9. The process according to claim 1 wherein the molar ratio of the halogenating reagent to the compound (I) is from about 2 to about 3.

10. The process according to claim 1 wherein the halogenation of the compound (II) is carried out in an inert organic solvent.

11. The process according to claim 10 wherein the inert organic solvent is diethyl ether, tetrahydrofuran, methylene chloride, ethylene dichloride, chloroform, carbon tetrachloride, benzene, or toluene.

12. The process according to claim 1 wherein an aqueous alkaline solution is a solution of an alkali or alkaline earth metal, or ammonium hydroxide, carbonate, bicarbonate, borate, or phosphate.

13. The process according to claim 1 wherein the salt of the compound (IV) is that with alkali or alkaline earth metal, or ammonium.

14. The process according to claim 1 wherein the polar aprotic solvent is dimethyl sulfoxide, N,N-dimethylformamide, or N,N-dimethylacetamide.

15. The process according to claim 1 wherein the molar ratio of the alkali metal salt of hydrogen sulfide or ammonium hydrogen sulfide to the compound (IV) or the salt thereof is from about 1 to about 6.

16. The process according to one of claims 1, 2 or 3 wherein the conversion of the halogen in the compound (IV) into the thiol group is carried out in an inert gas atmosphere.

17. The process according to claim 1 wherein the optically active β-hydroxyalkanoic acid (II) is the one prepared by subjecting the corresponding alkanoic acid to the stereospecific action of a microorganism.

18. The process according to claim 2 wherein the optically active β-hydroxyalkanoic acid (II) is the one prepared by subjecting isobutyric acid or methacrylic acid to the stereospecific action of a microorganism.

* * * * *